United States Patent
Rom

(10) Patent No.: US 7,894,902 B2
(45) Date of Patent: Feb. 22, 2011

(54) ADAPTIVE CARDIAC RESYNCRONIZATION THERAPY AND VAGAL STIMULATION SYSTEM

(76) Inventor: Rami Rom, 2 Hailan S, Or-akiva (IL) 30600

(*) Notice: Subject to any disclaimer, the term of this patent is extended or adjusted under 35 U.S.C. 154(b) by 521 days.

(21) Appl. No.: 11/817,228

(22) PCT Filed: Feb. 28, 2006

(86) PCT No.: PCT/IL2006/000265
§ 371 (c)(1), (2), (4) Date: Aug. 28, 2007

(87) PCT Pub. No.: WO2006/090397
PCT Pub. Date: Aug. 31, 2006

(65) Prior Publication Data
US 2008/0147130 A1    Jun. 19, 2008

(51) Int. Cl.
    *A61N 1/00* (2006.01)

(52) U.S. Cl. .................................................. 607/20
(58) Field of Classification Search .................. 607/9, 607/17, 20
    See application file for complete search history.

(56) References Cited

U.S. PATENT DOCUMENTS

| 7,657,313 B2* | 2/2010 | Rom ............................ 607/17 |
| 2002/0103512 A1* | 8/2002 | Echauz et al. ................. 607/9 |
| 2004/0215262 A1* | 10/2004 | Ferek-Petric ................ 607/17 |

* cited by examiner

Primary Examiner—George Manuel

(57) ABSTRACT

An adaptive feed-back controlled system for regulating a physiological function of a heart in which a hemodynamic sensor continuously monitors the physiological performance of the heart. Three implanted electrodes sense and pace the right atrial, right ventricle and left ventricle. A learning neural network module receives and processes information for the electrodes (18) and sensors (22), and is controlled by a deterministic module for limiting said learning module. A pulse generator (16), is also controlled by the deterministic module, and stimulates both the heart and the vagus (20).

6 Claims, 4 Drawing Sheets

ADAPTIVE CARDIAC RESYNCRONIZATION THERAPY AND VAGAL STIMULATION SYSTEM

FIELD OF THE INVENTION

The present invention relates generally to cardiac pacemakers and defibrillators and to central nerve system stimulators and more specifically to methods for optimising cardiac resynchronization therapy devices and vagal stimulators.

BACKGROUND OF THE INVENTION

Implanted pacemakers and intracardiac cardioverter defibrillators (ICD) deliver therapy to patients suffering from various heart-diseases (Clinical Cardiac Pacing and Defibrillation, $2^{nd}$ edition, Ellenbogen, Kay, Wilkoff, 2000). It is known that the cardiac output depends strongly on the left heart contraction in synchrony with the right heart (see U.S. Pat. No. 6,223,079). Congestive heart failure (CHF) is defined generally as the inability of the heart to deliver enough blood to meet the metabolic demand and it is often caused by electrical conduction defects. The overall result is a reduced blood stroke volume from the left side of the heart. For CHF patients, an installed permanent pacemaker with electrodes in 3 chambers that re-synchronize the left and right ventricles contractions provides an effective therapy, ("Device Therapy for Congestive Heart Failure", K. Ellenbogen et al, Elsevier Inc. (USA), 2004). The resynchronization task demands exact pacing management of the heart chambers such that the overall stroke volume is maximized for a given heart rate (HR), where it is known that the key point is to bring the left ventricle to contract in synchrony with the right ventricle. The re-synchronization task is patient dependent, and for each patient the best combination of pacing time intervals that restores synchrony are changed during the normal daily activities of the patient. Accordingly, a physiologically adaptive device is disclosed in WO 2005/007075, the contents of which are incorporated herein by reference, which changes the AV delay and VV interval dynamically, responding to inputs from hemodynamic sensors thus meeting the demand for auto-programmability and auto-adjustment.

However, cardiac pacemakers cannot slow down the natural atrial rate. They can increase the atrial rate by pacing the atria with a shorter VA interval (preceding the natural sinus rate) but cannot induce a prolonged VA interval. For congestive heart failure patients, slowing down the atrial rate can be a crucial requirement. For the failing heart, increasing the atrial rate does not produce a corresponding increase in the cardiac output, which may result in the brain impelling the heart to increase the rate, with no benefit. Even worse, more unproductive stress is generated in the failing heart as a result, and the condition may deteriorate.

Li M. et al in "Vagal nerve stimulation markedly improves long-term survival after chronic heart failure in rats", Circulation. 2004; 109:120-124, American Heart Association Inc. the contents of which are incorporated herein by reference, investigated the effects of chronic electrical stimulation of the vagus nerve on cardiac remodeling and long-term survival in an animal model of CHF after large myocardial infarction. Using an implantable miniature radio-controlled electrical stimulator, they stimulated the right vagal nerve of CHF rats for 6 weeks. The intensity of electrical stimulation was adjusted for each rat, so that the heart rate was lowered by 20 to 30 beats per minute. The treated rats had significantly lower left ventricular end-diastolic pressure and higher maximum dp/dt of left ventricular pressure than the untreated rats.

US Patent WO 2003/099377, discloses a vagus stimulator useful for slowing down the atrial rate in a controlled manner by stimulating the vagus nerve every heart beat in response to a triggering ECG feature (P wave for example) with a variable current amplitude and frequency. The vagus stimulation puts a limit to the atrial rate as pre-programmed whenever the atrial rate goes beyond a predefined limit. U.S. Pat. No. 5,330,507, the contents of which are incorporated herein by reference, discloses a vagal stimulation device within an implanted pacemaker device for the prevention and interruption of a life threatening arrhythmias. The device has two implanted heart leads, a right atrial and a right ventricle lead, and additionally two leads for stimulating the right or left vagus nerves. The implanted device monitors the electrograms of the heart, detects the atrial rate, the ventricular rates and the ST segment variations and response in the appropriate vagus nerve stimulation.

Vagal stimulation methods are used also for other clinical purposes such as preventing epilepsy seizures and ventricular rate regulation during atrial fibrillation. Such were disclosed in "Vagus Nerve Stimulation", by Diego Rielo, eMedicine, January 2006, the contents of which are incorporated herein by reference.

Selective atrioventricular nodal (AVN) vagal stimulation (AVN-VS) has emerged as a novel strategy for ventricular rate (VR) control in atrial fibrillation (AF). AVN-VS is delivered to the epicardial fat pad that projects parasympathetic nerve fibers to the AVN Although AVN-VS preserves the physiological ventricular activation sequence, the resulting rate is slow but irregular "Ventricular Rate Control by Selective Vagal Stimulation Is Superior to Rhythm Regularization by Atrioventricular Nodal Ablation and Pacing During Atrial Fibrillation", Shaowei Zhuang, et al, (Circulation. 2002; 106: 1853.). The authors indicate that the AVN-VS although producing a superior hemodynamic performance comparing to an ablation and pacing approach, results in irregular ventricular contractions similar to the effect of drug therapy. The negative effect is manifested in both prolonging the natural atrioventricular (AV) delay as well as causing some loss of synchrony with the underlying physiologically cardiac cycle timings identified through the irregular R-R intervals.

Tosato M., in "Heart Rate Control through Vagal Nerve Stimulation" $9^{th}$ Annual Conference Of the International RES Society, September 2004, Bournemouth, UK. discloses an external closed loop system for controlling the heart rate through vagal nerve stimulation that has influence on both the sinus atrial (SA) node and the atrioventricular (AV) node. Geddes L. et al. discuss in International Patent Application publication number WO 97/36637, the physiological effect on the SA and AV nodes of vagal stimulation as follows:—"The right vagus innervates the S-A node, the atrial muscle and, to a much lesser degree, the A-V node. The left vagus nerve innervates the S-A node and atrial muscle to a lesser degree than it innervates the A-V node. It is well known to physiologists that the stimulation of the right vagus nerve predominately slows the S-A node rate and thereby reduces heart rate. Stimulation of the left vagus nerve produces some slowing of the S-A node, prolongation of A-V conduction and partial or total A-V block."

With this asymmetrical influence of vagal stimulation on the SA and AV nodes cited above, it seems that vagal stimulation interfere with the fine correlation that exist in the cardiac cycle timings of the healthy heart where there is a known dependence of the AV delay on heart rate. Since AV synchrony is extremely important and loss of AV synchrony may be the cause of the pacemaker syndrome for example, the practicality of vagal stimulating is doubtful. It remains to be learned how the cardiac cycle timings and, for example, AV synchrony can be preserved if by stimulating the right vagii the heart rate slows down rate without affecting as much the AV node. Similarly, it remains to be learned how the left vagii can be stimulated, prolonging the AV delay without affecting the SA node and the heart rate. On the other hand if both vagii are stimulated is it known what should be the stimulation frequency or current amplitude relation between right and left vagii stimulations such that the influence on the AV node and SA node preserve the correlation between heart rate and AV delay of the healthy heart and does not cause a loss of AV synchrony for example?

Vagal stimulation is generally well tolerated but some patients experience pain, coughing, or hoarseness during stimulation. In addition, Jochen Springer in "Vagal Nerve Stimulation in Chronic Heart Failure: An Anti-inflammatory Intervention?", *Circulation*. 2004; 110:e34, argues that it is increasingly appreciated that efferent vagal nerve stimulation can also directly and rapidly regulate immune responses. It would appear, based on that observation, that having a system that on the one hand benefits from vagal stimulation and on the other hand minimizes the actual usage and intensity is a favourable solution to the problematic situation.

To summarize, vagal simulation is a clinical method under investigation and in practice although some difficulties are encountered in the implementation. The present invention combines cardiac resynchronization device with a vagal stimulation for treating heart failure patients and tries to benefit from the combined action of both devices so as to reduce the atrial rate by vagal stimulation and to improve the hemodynamic performance by resynchronization. In addition, since resynchronization increases the cardiac output it is expected that the heart rate should not increase as much as observed with untreated heart failure patients and hence the need and intensity of the vagal stimulation is expected to be lower comparing to a vagal stimulation device with no CRT device, and hence the combination of the two devices present here is expected to give additional advantages on top of each device therapy alone. And finally adaptive CRT device preserve AV synchrony at all heart rates in a closed loop system according to hemodynamic sensor, and hence a drawback of vagal stimulation which is loss of cardiac cycle timings and particularly the AV synchrony due to irregular R-R intervals may be cured by the present invention combined adaptive CRT and vagal stimulation system.

DETAILED DESCRIPTION OF THE PRESENT INVENTION

Figure 1:
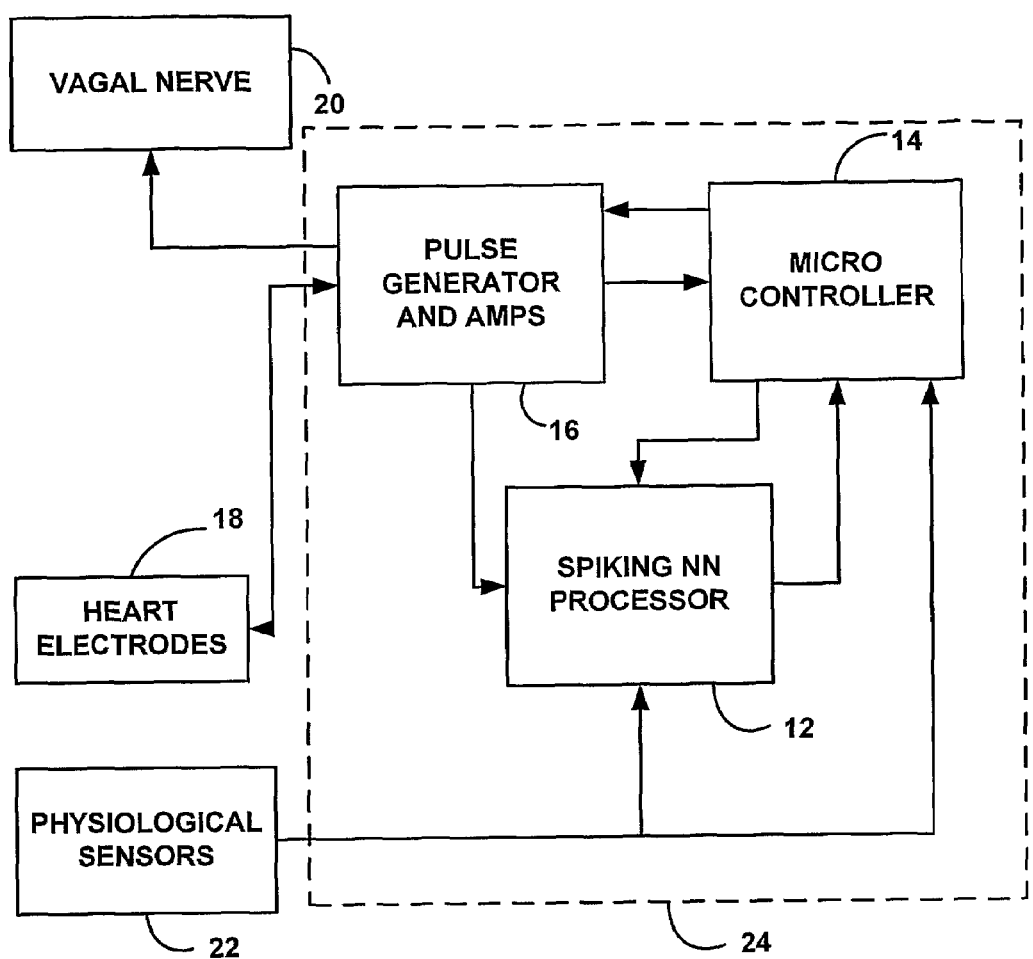
FIG. 1 is a schematic description of an adaptive CRT combined with a vagal stimulation device.

The present invention employs an implanted adaptive CRT system as described in a co-pending patent application by the same inventor published in WO 2005/007075. In the disclosed invention, both AV delay and the VV interval change dynamically in response to hemodynamic inputs from sensors in a closed loop system such that the stroke volume at a given heart rate is maximized online and continuously. This system therefore implies a feedback control. As described in FIG. 1 to which reference is now made, the device of the present invention is a combined adaptive CRT and vagal stimulator device. The spiking neural network processor (NNP) 12 includes the learning module, working as a slave processor of the micro-controller 14. A pulse generator and operational amplifiers 16, is the analogue interface to the electrodes implanted in the heart 18 of the patient, including the biventricular pacemaker, the right atria lead, right ventricular lead and left ventricular lead. An interface to the vagal nerve 20 lead is connected to pulse generator 16 as well. Three main output types of the NNP are AV delay, VV interval and vagal stimulation parameter. On the other hand, the NNP 12 receives IEGM (intracardiac electrogram) from controller 14. Physiological (hemodynamic) sensor 22 derives information relating to the patient, and feeds it to NNP 12 and controller 14. Unit 24 is implanted in the patient's body, in addition to electrodes and physiological other sensors 22.

Figure 2:
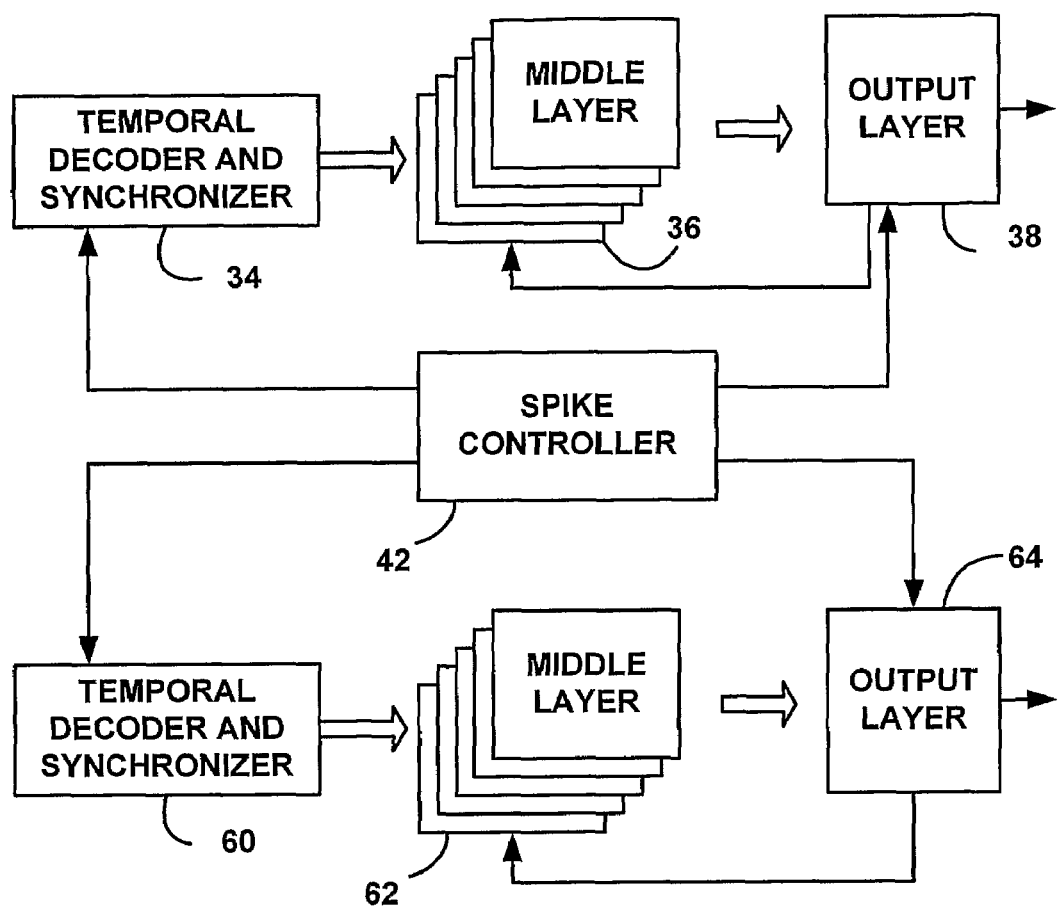
FIG. 2 is a schematic description of the spiking neural network architecture performing biventricular pacing and atrial rate regulation according to the intracardiac electrogram (IEGM) and hemodynamic (ventricular Impedance for example) sensors.

FIG. 2 shows in more detail the architectural aspects of NNP 12 that performs both biventricular pacing in response to hemodynamic sensors and atrial rate regulation. The first spiking neural network has three layers. An input layer with a temporal decoder and synchronizer 34, a middle layer 36, and an output layer 38. A spike controller 42 manages the neural network operations. The architecture of the second neural network is similar to the one described above. It optionally predicts the AV delay and VV pacing intervals, having a temporal decoder and synchronizer 60, a middle layer 62, and an output layer 64. The three important outputs of the learning module, the neural network processor, are AV delay, VV interval and the vagal stimulation current or frequency.

The adaptive CRT neural network processor architecture and its operation is as described in WO 2005/007075. In the present invention it is used in combination with a vagal nerve stimulator.

As mentioned above, the neural network for the atrial rate regulation has a similar architecture to the adaptive CRT neural network. The neural network spike controller, 12, manages both the adaptive CRT neural network operation and the atrial rate regulation neural network operation. The neural network task is to predict the vagal stimulation current amplitude or stimulation frequency that result in optimal heart rate sensed as the atrial rate, Atrial-Atrial (AA) Interval. The neural network architecture process both the IEGM (intracardiac electrogram) and the hemodynamic sensor input signal pattern that are also used for calculating cardiac output, which is obtained by multiplying the extracted stroke volume from the hemodynamic sensors by the heart rate.

Cardiac Output=Stroke Volume×Heart Rate.

Figure 3A:
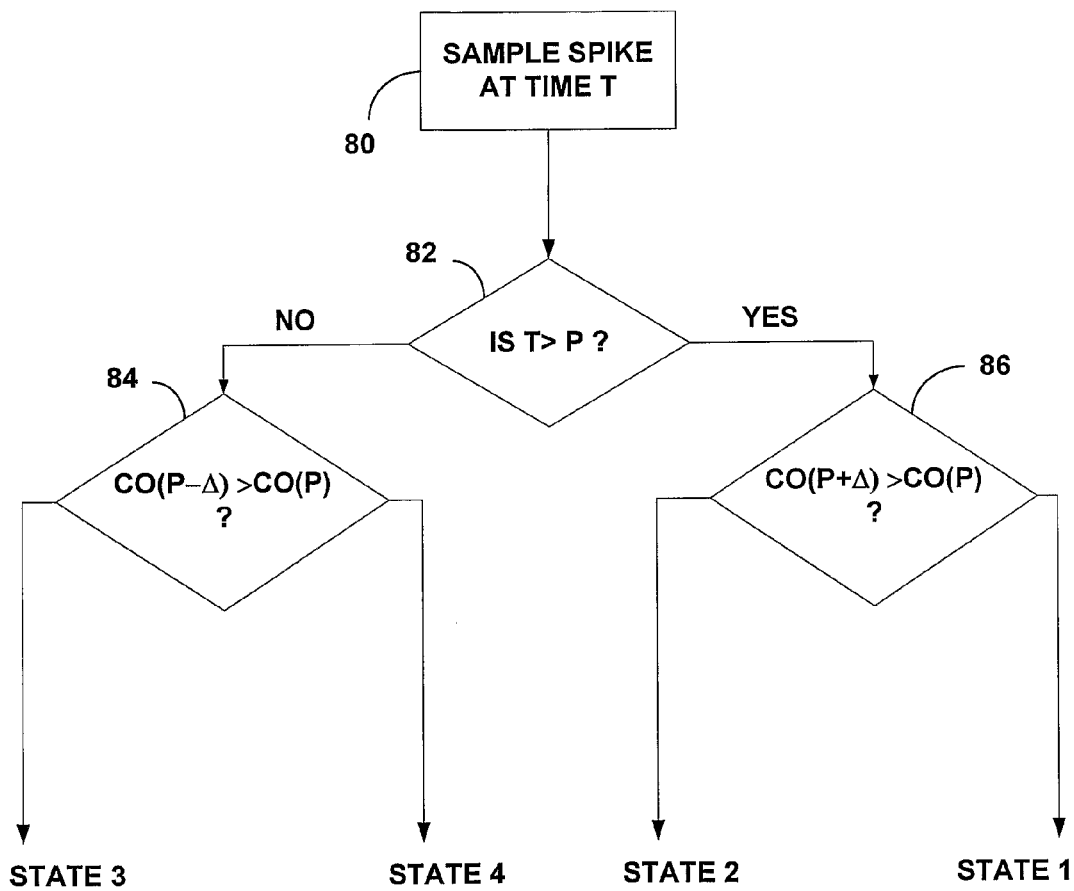
FIG. 3A is a flow chart showing the feedback control algorithm implemented in the system.

FIG. 3A shows the feedback control algorithm in a flow chart diagram. The feedback control algorithm is performed in two sequential steps in two consecutive cardiac cycles period. At first cycle 80, the timing of the integrate and fire (I&F) neuron firing relative to the previous atrial event, T, is sampled. Then T is compared to the time stored at the atrial-atrial pacing register, P, at step 82. If T is bigger then P the vagal stimulation current amplitude (or pulse duration) is lengthened in order to decrease the heart rate further, i.e. to increase the sensed A-A interval, whereas if T is smaller, P the vagal stimulation current amplitude (or pulse duration) is subsequently shortened in order to allow an increase the heart rate, i.e. to have a shorter A-A interval At the second cycle the cardiac output obtained with the new atrial-atrial interval, CO (P+/−ΔP) is compared with the previous cycle cardiac output CO (P). The results of the comparison define a particular state selected from 4 optional states in steps 86 and 84.

Figure 3B:
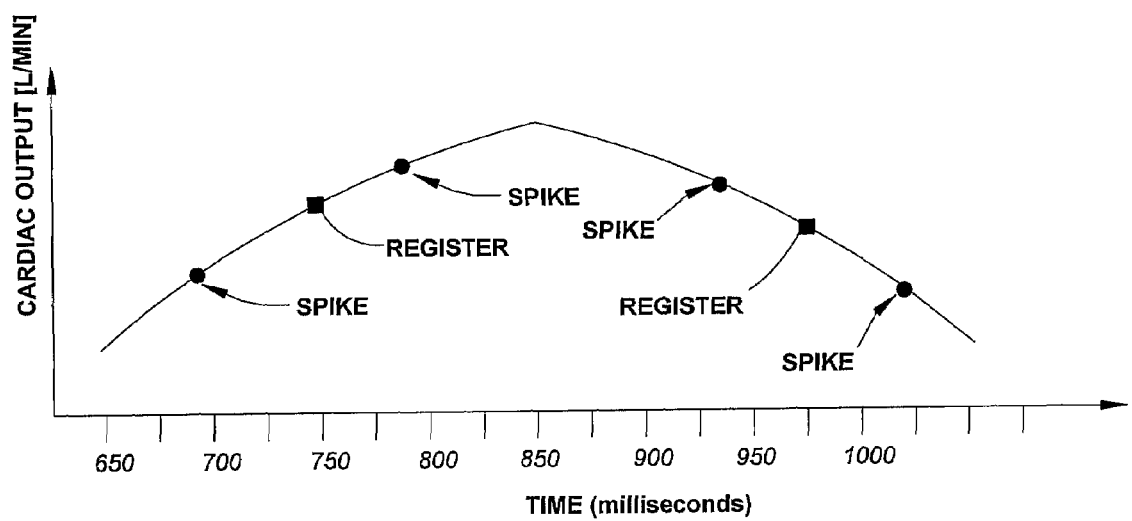
FIG. 3B is a cardiac output function of the atrial rate used in the feedback control algorithm.

FIG. 3B shows the way the synaptic weight are modified according to the states selected in FIG. 3A to which reference is again made and according to local information stored at each synapse, which is the internal synaptic state when the I&F neuron firing occurred at the first cardiac cycle. These synapse states are PRE HEBB, HEBB or POST HEBB. The definition of the internal synapse states are made according to the time each synapse is excited by temporal decoder 34 or 60 in FIG. 2 to which reference is again made. The four states shown in FIG. 3A to which reference is again made, are described in FIG. 3B on the bell shape curve, denoted are four possible scenarios on the bell shaped curve, and accordingly a decision is made at each synapse how to modify the internal synaptic weights in order to bring the firing time of the I&F neuron to occur at the maximal cardiac output curve. The synaptic weights Hebbian learning scheme shown in FIG. 3B is described in details in WO 2005/007075. With this feedback control algorithm, local synaptic weight Hebbian learning is combined with a global task of optimization of a function, which here is the cardiac output. The vagal stimulator receives the value of an atrial-atrial pacing register, which is changed dynamically as explained above, and increases or decreases the vagal nerve stimulation frequency, amplitude or pulse duration in order to bring the atrial rate to the neural network prediction of the best heart rate, the sensed atrial-atrial interval stored at the pacing register. Hence with the present invention the atrial rate is regulated dynamically by vagal stimulation and can be greater than the pre-programmed heart rate threshold parameter as long as the cardiac output is higher and satisfies better the metabolic demand of the patient.

Operating Modes

The adaptive CRT system disclosed in WO 2005/007075 alternates between two operational modes, a non-adaptive CRT and an adaptive CRT. In the non-adaptive CRT mode the pacing intervals, the AV delay and the VV interval are fixed as pre-programmed values whereas in the adaptive mode the AV delay and VV intervals are changed dynamically relating to the hemodynamic sensor. The complementary vagal stimulation of the present invention provides in addition a-vagal—on and a vagal-off operating modes. In the vagal-off mode, the adaptive CRT system operates as described in WO 2005/007075. In the vagal-on mode the vagal stimulation is applied and is optimized in a closed loop deriving reference from the calculated cardiac output extracted from hemodynamic sensor and the adaptive CRT device optimize the AV delay and VV interval at the same time as described above. The transition from vagal-off to vagal-on mode occurs when the heart rate crosses a pre-programmed heart rate threshold but in contrast to the vagal stimulation device described in WO 2003/099377 in the present invention in the vagal-on mode the heart rate is allowed to surpass the programmed limiting threshold as long it delivers a higher cardiac output and the combined adaptive CRT and vagal stimulation device regulates the heart rate as described above. Switching back to the vagal-off mode occurs when the heart rate crosses a pre-programmed threshold parameter, for example 100 beats per minute. The transition back and forth between adaptive and non-adaptive CRT mode is independent of the vagal-on and vagal-off operation modes. However the operation of the vagal stimulation in the vagal-on mode depends on the two CRT operation modes. When the combined device is operating in non-adaptive CRT mode the vagal-on mode will use the pre programmed threshold parameter for limiting the heart rate. Wherein adaptive CRT mode the heart rate threshold are be surpassed as described above.

Therefore, in the system of the present invention the atrial-atrial regulation is implemented continuously and online in the vagal-on mode, and concomitantly the adaptive CRT device performs the optimization of the biventricular pacing. In other word, the system optimizes the AV delay and VV interval in order to maximize the stroke volumes at a given heart rate as described in details in WO 2005/007075. The present invention, a combined adaptive CRT device and a vagal stimulator, maximizes the cardiac output by maximizing the stroke volumes and lowering the atrial rate as possible at the same time without lowering the total cardiac output.

In addition, the system in accordance with the present invention in contrast to the AVN-VS method presented in Zhuang et al. cited above, is able to preserve AV synchrony in all heart rates. This is due to the fact that the AV delay is optimized dynamically in a closed loop deriving reference from a hemodynamic sensor that reflects the ventricular function, and the optimal AV delay, and VV intervals, obtained are the optimal ventricular contractions timings that are the result of the underlying cardiac cycle, i.e. the best passive and active ventricular filling times at the diastolic cycle, and the best isovolumetric contraction and ejection timings during the systolic cycle.

The clinical benefit of the implementation of the present invention is manifested in better quality of life to CHF patients due to higher cardiac output achieved by the adaptive CRT device and of the heart function being improved by reducing the stress caused by excessive heart rates and by accurately synchronizing with the cardiac cycle timings. Such functional attributes have a long term effects, in improving the patient's heart condition.

Power Dissipation Considerations

The spiking neural network processor performs both the feedback control of the adaptive CRT device, i.e. changing dynamically the AV delay and VV pacing intervals in order to optimize the stroke volume, and the management of the atria rate with extremely low clock frequency of about 1 KHz. The spiking neural network processor performs the computation using a massively parallel neural network at a very low clock frequency, and the result is extremely low power dissipation, since the dynamic power dissipation in processors depends linearly on the clock frequency.

The invention claimed is:

1. An adaptive feed-back controlled system for regulating a physiological function of a heart, comprising:
    at least one hemodynamic sensor for continuously monitoring a significant physiological performance of the heart;
    three implanted electrodes for sensing and pacing the right atria, right ventricle and left ventricle;
    a learning neural network module for receiving and processing information of said at least one sensor;
    a deterministic module for controlling and limiting said learning module, and
    at least one pulse generator controlled by said deterministic module for stimulating both the heart and the vagus nerve.

2. A system according to claim 1 wherein said modules and therapeutic delivery means are, delivering adaptive biventricular stimulation to the heart with dynamic AV delay and VV interval, wherein said stimulation is modified continuously in correlation with the hemodynamic performance of the heart, combined with a vagal stimulator that slows down the atrial rate by stimulating the vagus nerve and wherein the combined system preserve AV synchrony and cardiac cycle optimal timings.

3. A system according to claim 1 wherein said neural network module employs a spiking neuron network architecture implemented in a processor operating with low clock frequency at the range 1-10 KHz and with synaptic weight adaptation deriving reference from a hemodynamic sensor input and implementing a Hebbian learning rule.

4. A method of regulating a controlled delivery of a physiologically active agent to a patient comprising the steps of:
  obtaining continuous signal from at least one sensor monitoring at least one physiological parameter of said patient;
  processing said at least one continuous signal using an algorithmic processing module and a learning module, and wherein said learning module carries out adaptive learning in connection with said at least one sensor, wherein said learning is controlled and supervised by said algorithmic module, and
  delivering a physiological signal by a delivery module in response to said processed signal, wherein said delivery module is controlled by said algorithmic module;
  programming initial AV (atrioventricular) delay parameter VV (interventricular delay) interval parameter and a heart rate threshold parameter of said algorithmic module;
  switching to a vagal-on mode whenever the sensed heart rate exceeds said programmed heart rate threshold parameter;
  switching back to vagal-off mode when the sensed heart rate is lower than the pre-programmed heart rate threshold parameter;
  providing pacing in a non-adaptive CRT mode whereby pacing is provided according to said pre-programmed AV delay and VV interval parameters;
  switching to an adaptive CRT mode wherein said AV delay and VV interval change dynamically in order to achieve optimal hemodynamic performance, and wherein said adaptive mode is limited to perform above a low limit of hemodynamic performance, and
  switching back to the non-adaptive CRT mode whenever the hemodynamic performance drops below a low limit of hemodynamic performance or a sensor failure or any other system failure is detected.

5. A method of regulating a controlled delivery of a physiologically active agent to a patient as in claim 4 wherein said vagal stimulation is provided in said adaptive and said non-adaptive CRT mode.

6. A method of regulating a controlled delivery of a physiologically active agent to a patient as in claim 4 wherein the current amplitude and frequency of said vagal stimulation are modified to optimize the sensed heart rate with reference to a neural network processor prediction, wherein the programmed heart rate threshold parameter in said adaptive CRT mode is larger than the heart rate threshold parameter in said non-adaptive CRT mode.

* * * * *